US007229620B2

(12) United States Patent
Chinn

(10) Patent No.: US 7,229,620 B2
(45) Date of Patent: *Jun. 12, 2007

(54) METHOD FOR RADIOLABELING ANTIBODIES WITH YTTRIUM-90

(75) Inventor: Paul Chinn, Carlsbad, CA (US)

(73) Assignee: Biogen Idec Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/181,811

(22) Filed: Jul. 15, 2005

(65) Prior Publication Data

US 2006/0067884 A1 Mar. 30, 2006

Related U.S. Application Data

(63) Continuation of application No. 09/628,186, filed on Jul. 28, 2000, now Pat. No. 6,994,840, which is a continuation of application No. 09/259,338, filed on Mar. 1, 1999, now abandoned.

(51) Int. Cl.
*A61K 39/395* (2006.01)

(52) U.S. Cl. .................. 424/179.1; 424/1.53; 424/1.69; 530/391.5

(58) Field of Classification Search ............... 424/1.53, 424/1.69, 179.1; 530/391.5
See application file for complete search history.

(56) References Cited

U.S. PATENT DOCUMENTS

| | | | |
|---|---|---|---|
| 4,401,592 A | 8/1983 | Yoshikumi et al. | |
| 4,636,380 A | 1/1987 | Wong | |
| 4,816,567 A | 3/1989 | Cabilly | |
| 5,124,471 A | 6/1992 | Gansow et al. | |
| 5,434,287 A | 7/1995 | Gansow et al. | |
| 5,460,785 A | 10/1995 | Rhodes | |
| 5,500,362 A | 3/1996 | Robinson et al. | |
| 5,541,287 A | 7/1996 | Yau | |
| 5,595,721 A | 1/1997 | Kaminski et al. | |
| 5,728,369 A | 3/1998 | Griffiths | |
| 5,736,137 A * | 4/1998 | Anderson et al. | ........ 424/133.1 |
| 5,766,751 A | 6/1998 | Kotani et al. | |
| 5,820,845 A | 10/1998 | Dean et al. | |
| 5,830,431 A | 11/1998 | Srinivasan et al. | |
| 5,874,540 A | 2/1999 | Hansen et al. | |
| 6,994,840 B1 * | 2/2006 | Chinn | ....................... 424/1.53 |

FOREIGN PATENT DOCUMENTS

| | | |
|---|---|---|
| EP | 0 274 394 | 7/1988 |
| EP | 0 529 645 A | 3/1993 |
| WO | WO 88/04936 | 7/1988 |
| WO | WO 92/07466 | 5/1992 |
| WO | WO 94 11026 A | 5/1994 |
| WO | WO 96/14879 | 5/1996 |

OTHER PUBLICATIONS

Gansow et al., Advanced Methods for Radiolabeling Monoclonal Antibodies with Therapeutic Radionuclides, *Cancer Therapy With Radiolabelled Antibodies*, 1995, Chpater 6, pp. 63-76.
Gary L. Griffiths, Antibody Radiolabeling With Isotopes of Rhenium, *Cancer Therapy With Radiolabelled Antibodies*, 1995, Chapter 7, pp. 77-86.
Adams RA, "Formal Discussion: The role of transplantation in the experimental investigation of human leukemia and lymphoma," *Cancer Research*, 1967, 27(1):2479-2482.
Adams RA, et al., "Direct implantation and transplantation of human acute lymphoblastic leukemia in hamsters, SB-2," 1968, *Cancer Research*, 1968, 28:1121-1125.
Chakrabarti MC et al., "Prevention of radiolysis of monoclonal antibody during labeling," *J. Nucl. Med.*, 1996, 37(8):1384-88.
DeNardo et al., "Yttrium-90/Indium-111 DOTA peptide chimeric L6: pharmacokinetics, dosimetry and initial therapeutic studies in patients with breast cancer," J. Nucl. Med., 1995, 36:97P.
Kozak RW, et al., "Nature of the bifunctional chelating agent used for radioimmunotherapy with yttrium-90 monoclonal antibodies: critical factors in determining in vivo survival and organ toxicity," Cancer Res., 1989, 49(10):2639-44.
Leland JK, et al., "Electrogenerated chemiluminescence: An oxidative-reduction type ECL reaction sequence using Tripropyl Amine," *Electrochem. Soc.*, 1990, 137, 3127.
Lewis et al., "A facile, water-soluble method for modification of proteins with DOTA," *Bioconj Chem.*, 1994, 5:565-76.
Lindmo T, et al., "Determination of the immunoreactive fraction of radiolabeled monoclonal antibodies by linear extrapolation to binding at infinite antigen excess," J Immunol Methods, 1984, 72(1):77-89.
Liu AY, et al., "Production of a mouse-human chimeric monoclonal antibody to CD20 with potent Fc-dependent biologic activity," J. Immunol., 1987, 139/10:3521-26.
Mather SJ, et al., "Labeling monoclonal antibodies with yttrium-90," Eur. J. Nucl. Med., 1989, 15;307-312.
Mirzadeh S., et al., "Radiometal labelling of immunoproteins: Covalent linkage of 2-(4-Isothiocyanatobenzyl)diethylenetriaminepentaacetic acid ligands to immunoglobulin," *Bioconj Chemistry*, 1990, 1(1):59.
Muller RJ, "Calculation of average antibody affinity in anti-hapten sera from data obtained by competitive radioimmunoassay," J Immunol Methods, 1980, 34(4):345-52.

(Continued)

*Primary Examiner*—David A. Saunders
(74) *Attorney, Agent, or Firm*—Pillsbury Winthrop Shaw Pittman LLP

(57) ABSTRACT

Methods and kits for radiolabeling proteins, peptides and ligands with radiolytic isotopes, particularly yttrium-90, are disclosed, whereby sufficient purity, specific activity and binding affinity are achieved such that the radiolabeled protein may be directly administered to a patient without further column purification. Such kits and methods will be particularly useful in bringing radioimmunotherapy to the hospital and outpatient setting for the treatment of cancer.

20 Claims, 1 Drawing Sheet

OTHER PUBLICATIONS

Parker BA, et al., "Radioimmunotherapy of human B-cell lymphoma with 90Y-conjugated antiidiotype monoclonal antibody," *Cancer Research*, 1992, 50:1022s-28s.

Pietersz GA, et al., "The use of monoclonal antibody conjugates for the diagnosis and treatment of cancer," Immunol. Cell Biol., 1987, 65:111-125.

Pizzarello, Direct and indirect action. In Pizzarello and Witcofski, eds. *Basic Radiation Biology*, 2nd ed. Philadelphia: Lea & Febger, 1975, pp. 20-29.

Robinson, RD et al., "Chimeric mouse-human anti-carcinoma antibodies that mediate different anti-tumor cell biological activities," Hum. Antibod. Hybridomas, 1991, 2:84-93.

Salako et al., "Effects of radiolysis on yttrium-90-labeled Lym-1 antibody preparations," J. Nucl. Med., 1998, 39:667-70.

Thomas et al., Gamma-interferon administration after 90Y radiolabeled antibody therapy: survival and hematopoietic toxicity studies," Int. J. radiat. Oncol. Biol. Phys., 1995, 31:529-534.

Brechbiel MW, et al., "Synthesis of 1-(p-Isothiocyanatobenzyl) derivatives of DPTA and EDTA. Antibody labeling and tumor-imaging studies," *Inorganic Chemistry*, 1986, 25(16):2772-81.

Chinol et al, "Generator-Produced Yttrium-90 for Radioimmunotherapy," J. Nuclear Medicine, 1987, 28(9):1465-1470.

Hnatowich et al., "The Preparation of DTPA-Coupled Antibodies Radiolabeled with Metallic Radionuclides: an Improved Method," J. Immunological Methods, 1983, 65:147-157.

Cytogen OncoScint Product Information, 1998, Internet document.

Richardson et al., Optimization and batch production of DTPA-labeled antibody kits for routine use in $^{111}$in immunoscintography, Nuclear Medicine Communications, 1987, 8:346-356.

Goodwin et al., "Chelate Conjugates of Monoclonal Antibodies for Imaging Lymphoid Structures in the Mouse," 1985, 26(5):493-498.

International Search Report for PCT/US00/05078, mailed Dec. 28, 2000.

International Preliminary Examination Report for PCT/US00/05078, mailed Jul. 12, 2001.

International Search Report for PCT/US00/05061, mailed Dec. 12, 2000.

International Preliminary Examination Report for PCT/US00/05061, mailed May 4, 2001.

\* cited by examiner

Binding of Y2B8 to CD20-Positive Cells

METHOD FOR RADIOLABELING ANTIBODIES WITH YTTRIUM-90

CROSS RELATED APPLICATIONS

This is a continuation of U.S. patent application Ser. No. 09/628,186, filed Jul. 28, 2000, now U.S. Pat. No. 6,994,840 B1 issued on Feb. 7, 2006, which is a continuation of U.S. patent application Ser. No. 09/259,338, filed Mar. 1, 1999, now abandoned, all of which are incorporated by reference in their entirety.

FIELD OF THE INVENTION

The present invention relates to kits and methods for radiolabeling proteins, peptides and ligands with therapeutic radioisotopes such that these radiolabeled agents may be administered directly to patients without the need for additional purification. Such kits and methods are particularly applicable to labeling proteins and peptides with yttrium-90 ($^{90}Y$). By optimizing the radiolabeling protocol such that no further purification of the radiolabeled protein is required, the present invention has satisfied a long-felt need in the art by solving the persistent problem of how to provide yttrium-labeled drugs in a user-friendly format such that these drugs may be easily prepared and administered in the hospital or outpatient setting.

TECHNOLOGY BACKGROUND

All publications and patent applications herein are incorporated by reference to the same extent as if each individual publication or patent application was specifically and individually indicated to be incorporated by reference.

Radiolabeled proteins, particularly antibodies, have been undergoing evaluation for many years as potential diagnostic and therapeutic reagents. Such reagents are thought to be particularly useful as cancer therapeutics, now that researchers are beginning to identify tumor-specific antigens and cognate ligands or antibodies which bind to such antigens. By administering a radiolabeled ligand or antibody which has binding specificity for a tumor-specific antigen, coupled to a radioisotope that has a short range, high energy and abundant particle emission, one has the potential to deliver a lethal dose of radiation directly to the tumor cell.

Depending on the particle range of the particular isotope, labels may be chosen based on their suitability for targeting a particular type of cell. For instance, gamma emitters are generally used for diagnostic purposes, i.e., visualizing tumors, but are generally ineffective as killing agents. In contrast, alpha and beta emitters may be used to effect cell killing. Alpha emitters may be particularly useful for bloodborn diseases or vascular tumors where they can achieve good penetration; although one particle emission in some cases may be enough to effect cell killing, typically alpha emitter must be located right at the cell surface. In contrast, beta emitters, i.e., $^{90}Y$, are particularly suitable for bulkier, more localized disease because they typically have a longer emission range.

Yttrium-90-labeled antibodies and peptides in particular have shown encouraging results in clinical therapy protocols (Thomas et al. 1995. Gamma-interferon administration after $^{90}Y$ radiolabeled antibody therapy: survival and hematopoietic toxicity studies. Int. J. Radiat. Oncol. Biol. Phys. 31: 529–534; DeNardo et al. 1995. Yttrium-90/Indium-111 DOTA peptide chimeric L6: pharmacokinetics, dosimetry and initial therapeutic studies in patients with breast cancer. J. Nucl. Med. 36: 97P). Such conjugates are usually made by coupling a bifunctional chelator to the protein or antibody, then conjugating the radiolabel to the protein construct via the bifunctional chelator. For instance, copending application Ser. Nos. 08/475,813, 08/475,815 and 08/478,967, herein incorporated by reference, describe radiolabeled therapeutic antibodies for the targeting and destruction of B cell lymphomas and tumor cells. Particularly disclosed is the Y2B8 conjugate, which comprises an anti-human CD20 murine monoclonal antibody, 2B8, attached to $^{90}Y$ via a bifunctional chelator, MX-DTPA.

Patents relating to chelators and chelator conjugates are known in the art. For instance, U.S. Pat. No. 4,831,175 of Gansow is directed to polysubstituted diethylenetriaminepentaacetic acid chelators and protein conjugates containing the same, and methods for their preparation. U.S. Pat. Nos. 5,099,069, 5,246,692, 5,286,850, and 5,124,471 of Gansow also relate to polysubstituted DTPA chelators. As described in Kozak et al., several DTPA chelating agents, including MX-DTPA, have been shown to be suitable for yttrium-monoclonal antibody radioimmunotherapy (1989. Nature of the bifunctional chelating agent used for radioimmunotherapy with yttrium-90 monoclonal antibodies: Critical factors in determining in vivo survival and organ toxicity. Cancer Res. 49: 2639–2644). These references are incorporated herein in their entirety.

Yttrium-90 is particularly suited for radioimmunotherapy and radioligand therapy for several reasons. The 64 hour half-life of $^{90}Y$ is long enough to allow antibody accumulation by the tumor and, unlike e.g., $^{131}I$, it is a pure beta emitter of high energy (E max 2.27 MeV) with no accompanying gamma irradiation in its decay. It's particle emission range is 100 to 1000 cell diameters, which is a sufficiently minimal amount of penetrating radiation that outpatient administration would be possible. Furthermore, internalization of labeled antibodies is not required for cell killing, and the local emission of ionizing radiation should be lethal for adjacent tumor cells which might lack the target antigen.

However, despite the recognized utility of yttrium-labeled antibodies and the encouraging clinical results with some yttrium-labeled therapeutics, many patients are deprived of the benefit these therapeutics might offer because of the inherent difficulties in conducting both the radiolabeling and administration at a single location. This significant problem is evident in the nearly complete void of kits and products which enable on-site labeling of reagents with alpha and beta emitting radioisotopes, which might otherwise demonstrate the commercial applicability of such technology.

The problem with providing kits for radiolabeling and subsequent administration of therapeutics labeled with destructive isotopes appears to be the long-existing belief in the art that, before such therapeutics could be administered to a patient, an extensive purification process was required to remove unbound label so as not to expose the patient to free radioisotope which might accumulate in the bone and other non-target organs. Even those kits currently available for labeling antibodies with yttrium require a complicated purification step before the therapeutic is ready for administration.

For instance, Antisoma currently offers a kit for radiolabeling monoclonal antibody HMFG1 (Theragyn®) with $^{90}Y$ for subsequent administration to patients who have been diagnosed with ovarian cancer. An extended phase I–II study demonstrated that this treatment may be particularly beneficial to patients as a follow-up to conventional surgery and chemotherapy (Hird et al. 1993. Adjuvant therapy of ovarian cancer with radioactive monoclonal antibody. Br. J. Cancer 68: 403–406). Yet Antisoma's labeling method requires removal of unbound label by Sephadex G50 gel filtration, which is a significant deterrent to the Theragyn® labeling kit achieving commercial success, as well as an obstacle for ensuring that this therapy is readily available for all ovarian cancer patients for whom it might serve to benefit.

The fact that such reagents currently require purification before administration has been and will continue to be a major deterrent in their availability to all patients who could benefit from such technology unless a simplified method is presented that allows physicians to quickly, efficiently and safely administer such reagents. For instance, a doctor in an outpatient setting does not have the time or facilities to purify a reagent by HPLC or gel filtration chromatography before administering the reagent to his patient. This means that additional facilities must be available on site for concurrent production of the reagent and immediate delivery to the doctor, which drastically increases the cost of the therapy and in some cases might require a patient to travel a significant distance to receive the therapy. Alternatively, the drug could be labeled off-site, which would require prior preparation and at least a short-term storage of the therapeutic. This not only has the effect of decreasing the strength of the radioisotope through radioactive decay during storage, but also leads to significant radiolytic damage to the structural integrity of the protein by overexposure to the radioisotope.

For instance, many reports have discussed the radiolytic nature of $^{90}Y$ and similar radioisotopes (i.e., Salako et al. 1998. Effects of radiolysis on yttrium-90-labeled Lym-1 antibody preparations. J. Nucl. Med. 39: 667–670; Chakrabarti et al. 1996. Prevention of radiolysis of monoclonal antibody during labeling. J. Nucl. Med. 37: 1384–1388). As noted in Chakrabarti et al., radionuclides such as $^{90}Y$ deliver a large amount of radiation to the antibody during the labeling process as well as during storage. Radiation has reportedly led to instances of significant antibody damage, which can eliminate preferential targeting of tumor cells and expose non-target tissues to significant levels of toxicity.

The mechanism for radiation damage has been attributed to the generation of free radicals (Pizzarello. 1975. Direct and indirect action. In: Pizzarello and Witcofski, eds. *Basic Radiation Biology*, $2^{nd}$ ed. Philadelphia: Lea & Febger, pp. 20–29). But as noted in Salako et al., at an energy of 2.2 MeV, the beta particles emitted from $^{90}Y$ could easily break most chemical bonds including the disulfide bridges of an antibody, which have a bond strength of only 4.4 eV (Skoog. 1985. *Principles of Instrumental Analysis*, $3^{rd}$ edition. San Francisco: Saunders). Thus, the shorter the amount of time that the protein to be labeled is exposed to destructive radioisotopes such as $^{90}Y$, the better the chances will be that the protein will maintain the structural integrity and binding specificity it requires to interact with the target antigen up until the time it is administered and reaches the target site.

The radiolytic nature of $^{90}Y$ has been known in the art for years and many have tried to solve the problem $^{90}Y$ presents in the commercial application of these therapeutics. For instance, both Salako et al. and Chakrabarti et al. evaluate the use of radioprotectants in $^{90}Y$-labeled antibody preparations as a means to decrease damage to the antibody. Salako et al. in particular reported that human serum albumin enabled maintenance of $^{90}Y$-labeled antibody immunoreactivity for up to 72 hours. However, the specific activity exhibited by Salako's preparations was rather low (less than 2 mCi/ml). Moreover, neither Salako nor Chakrabarti report any effort to forego the extensive purification processes required after antibody labeling. Salako et al. labels for a period of 45 minutes to an hour, then purifies the antibody by molecular sieve chromatography, whereas Chakrabarti labels for nearly three hours and purifies by gel filtration chromatography. Neither of these methods will be instrumental in bringing $^{90}Y$-labeled therapeutics to the outpatient setting.

Chinol and Hnatowich were able to achieve 90% radiochemical purity for $^{90}Y$-labeled proteins with specific activities ranging from 1–3 mCi/mg absent post-labeling purification, using their own generator-produced $^{90}Y$ (1987. Generator-produced yttrium-90 for radioimmunotherapy. J. Nucl. Med. 28(9): 1465–1470). However, the authors expressly discourage administering preparations having less than 95% purity to patients, and suggest that HPLC may be an important and "possibly essential" step.

Those who have recognized that HPLC and other types of purification must be eliminated in the outpatient and hospital setting have not succeeded in developing a sufficient labeling protocol for $^{90}Y$ such that a high level of label incorporation is achieved and an acceptable level of antibody stability is maintained. If a high level of radioincorporation is not consistently achieved, the patient could be exposed to unacceptable levels of free non-bound radiolabel if this label is not purified away from the reagent. Moreover, again, if antibody structural integrity is damaged such that the antibody loses target specificity, such reagents will not bind specifically to their cognate ligands.

Mather and colleagues set out with the purpose of labeling tumor-specific antibodies with $^{90}Y$ in a manner such that post-labeling purification could be avoided (1989. Labeling monoclonal antibodies with yttrium-90. Eur. J. Nucl. Med. 15: 307–312). However, Mather found that high labeling efficiencies (over 95%) could only be achieved at modest specific activities (1 mCi/mg). Moreover, Mather et al. reports that their antibody preparations showed signs of breakdown (due to radiolysis) after only a few hours. This may be because Mather et al., as do many others in the field, conducted their labeling reaction over a period of one hour.

For example, there have been methods proposed for labeling protein reagents with less destructive labels such as $^{111}In$ which forego additional purification steps. Richardson et al. propose such a procedure for labeling antibodies with $^{111}In$ with the goal of facilitating a kit format for diagnostic use (Richardson et al. 1987. Optimization and batch production of DTPA-labeled antibody kits for routine use in $^{111}In$ immunoscintography. Nucl. Med. Comm. 8: 347–356). However, the labeling method proposed in Richardson et al. is conducted over a period of one hour, which might be feasible with $^{111}In$ which is not very radiolytic, but does not appear to be amenable to $^{90}Y$ labeling applications as evidenced by the difficulties reported in Mather et al.

This brings us to the surprising and unexpected advantages of the present invention, which provides invaluable insight into the process of radiolabeling proteins with $^{90}Y$ which has not been yet been recognized by others in the art. Surprisingly, the present inventors have found that the processes of HPLC or other purification steps that others have long thought to be necessary to achieve pure reagent, and the lengthy incubation times which others have adopted in an effort to increase the specific activity of their reagents, are actually detrimental to the process of preparing $^{90}Y$-labeled reagents. Such time-inclusive processes serve only to increase the damage to the protein due to radiolysis, leading to less specificity or binding, loss of radioisotope from the targeting agent and an increased rate of protein degradation by the time the radiolabeled protein is ready for injection. Surprisingly, the present inventors have found that efficient labeling with $^{90}$Y (>95% incorporation and at least 15 mCi/mg specific activity) can be accomplished in as little as two to five minutes, and in fact such labeling loses its efficiency as reaction times are increased beyond even eight minutes.

The fact that labeling with $^{90}$Y may now be achieved by the methods of the present invention in as little as one-two minutes or even as quickly as 30 seconds will completely dissolve the current skepticism in the field toward the applicability of yttrium radiolabeling kits in hospital and outpatient settings. The kits of the present invention will therefor finally satisfy the long felt need that has perhaps been recognized by many cancer patients and doctors alike with regard to the commercial applicability and accessability of protein-based, radiolabeled cancer therapeutics.

SUMMARY OF THE INVENTION

The present invention concerns methods and kits for radiolabeling a chelator-conjugated protein or peptide with a therapeutic radioisotope for administration to a patient. The methods of the present invention essentially comprise (i) mixing the chelator-conjugated protein, ligand or peptide with a solution comprising the radioisotope or a salt thereof, and (ii) incubating the mixture for a sufficient amount of time under amiable conditions such that a radiolabeled protein or peptide having sufficient purity, i.e., level of radioincorporation, specific activity and binding specificity is achieved such that the radiolabeled antibody may be administered directly to the patient without further purification.

The kits of the present invention essentially comprise (i) a vial containing chelator-conjugated protein or peptide, (ii) a vial containing formulation buffer for stabilizing and administering the radiolabeled antibody to a patient, and (iii) instructions for performing the radiolabeling procedure, such that when the chelator-conjugated protein or peptide is exposed to the radioisotope or a salt thereof for a sufficient amount of time under amiable conditions as recommended in said instructions, a radiolabeled protein or peptide having sufficient purity, specific activity and binding specificity is achieved such that the radiolabeled antibody may be diluted to an appropriate concentration in said formulation buffer and administered directly to the patient without further purification. It be noted that the sterile vial format of the disclosed kits also forego the need for sterility or endotoxin testing, thereby further simplifying the kit and making it more user-friendly.

DETAILED DESCRIPTION OF THE INVENTION

Figure 1:
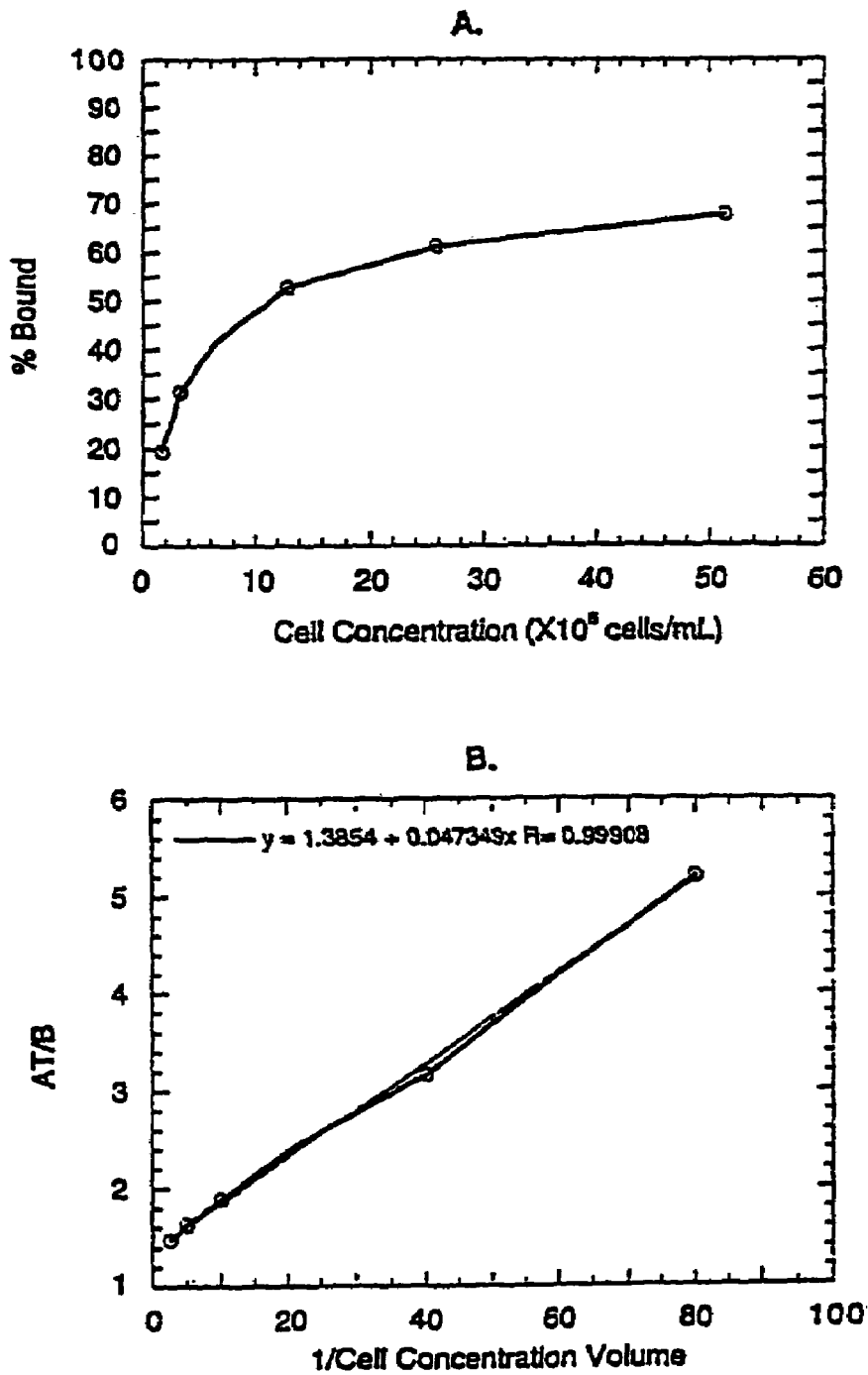
FIG. 1. A) SB cells were washed and resuspended to $90 \times 10^6$ cells/mL with dilution buffer (1× PBS, pH 7.4 containing 1% (w/v) bovine serum albumin. Increasing concentrations of cells were incubated for 3 h with 2 ng/mL Y2B8 prepared using 2B8-MX-DTPA lot # 0165A. B) Double-inverse plot of cell concentration vs. bound radioactivity/total radioactivity (B/AT). Immunoreactivity was calculated as 1/y-intercept×100. Immunoreactivity and correlation coefficient (R) values were 72.2% and 0.999, respectively.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The present invention includes a method for radiolabeling a chelator-conjugated protein, ligand or peptide with a therapeutic radioisotope for administration to a patient comprising (i) mixing the chelator-conjugated protein or peptide with a solution comprising the radioisotope or a salt thereof, and (ii) incubating the mixture for a sufficient amount of time under amiable conditions such that a radiolabeled protein or peptide having sufficient purity, i.e., level of radioincorporation, specific activity and binding specificity is achieved such that the radiolabeled antibody may be administered directly to the patient without further purification. "Further purification" includes HPLC, gel filtration, other types of column chromatography and any other separation technique which is employed with the purpose of removing free or bound unconjugated radiolabel.

The methods of the present invention are particularly applicable to therapeutic radioisotopes which are typically radiolytic and therefor potentially dangerous to the structural integrity of the protein. Such therapeutic radioisotopes are generally selected from the group consisting of alpha and beta emitters. Preferred therapeutic radionuclides include $^{203}$Pb, $^{212}$Pb $^{212}$Bi $^{109}$Pd $^{64}$Cu, $^{67}$Cu, $^{90}$Y, $^{77}$Br, $^{211}$At, $^{97}$Ru, $^{105}$Rh, $^{195}$Au and $^{199}$Ag or $^{177}$Lu. Other radionuclides which have therapeutic utility are described in U.S. Pat. No. 5,541,287, herein incorporated by reference. Particularly preferred radionuclides are strong beta radiation emitters which may cause intramolecular decomposition, such as $^{90}$Y, $^{67}$Cu, $^{131}$I, $^{186}$Re and $^{188}$Re. Although a "therapeutic" radioisotope generally refers to radioisotopes such as beta and gamma emitters which have a cytotoxic affect, to the extent that such radioisotopes may also be used for diagnostic purposes, such purposes do not remove these isotopes from the scope of the present invention because it is the radiolytic nature of these isotopes which renders them suitable for the disclosed methods and kits.

The methods of the present invention may be used to label proteins, ligands or peptides, particularly protein ligands where structural integrity must be maintained for target specificity. Preferred proteins are antibodies or antibody fragments, such as Fab, (Fab)$_2$, and Fv fragments, which recognize tumor specific or tumor-associated antigens. Preferred peptides include somatostatin, vasointestinal peptide (VIP), substance P and others which bind to cellular receptors. Such peptides and chelator-conjugated derivatives of such peptides are disclosed in U.S. Pat. No. 5,830,431, herein incorporated by reference.

A "sufficient incubation time" as referenced in the methods of the invention is the acceptable time range during which sufficient radioincorporation and radiochemical purity are achieved such that the reagent may be administered directly to a patient without the need for further purification. Sufficient radioincorporation and purity is generally recognized in the art to be at least 95%, but may vary depending on the toxicity of the label. It should also be apparent to those of skill in the art that the extent of radioincorporation considered to be sufficient is also a function of the desired level of efficacy. For $^{90}$Y, and particularly the $^{90}$Y-labeled antibodies of the present invention, such sufficient time may be generally less than about eight minutes, and more preferably between about two to about five minutes, given an amenable molar ratio of chelator to protein in the chelator-conjugated protein to be labeled.

It should be apparent to those of skill in the art that the optimum time required for labeling a specific protein may vary depending on the protein, the particular radiolabel and the particular conjugate employed. An underlying factor in the optimization of the time allotted for radiolabeling is the chelator to protein ratio of the reagent which is to be labeled. For instance, the chelator to protein ratio must be high enough to achieve a therapeutically useful level of incorporation, i.e., 95%, but must also not be too high such that the structural integrity or immunoreactivity of the protein is compromised. This requires a certain balancing process that in some cases may lead to a lower level of conjugated chelator and longer labeling time.

For instance, the present inventors have discovered that labeling with $^{90}Y$ to the desirable level of purity may be accomplished in under five minutes using MX-DTPA as a chelator and only about a 1½ to 1 molar ratio of chelator to antibody. Although the chelator to antibody ratio could actually be increased, this was not necessary because a desirable level of radioincorporation and specific activity was achieved after a short labeling period. Given this discovery, parameters such as chelator to protein concentrations could be readily determined by empirical means by those of skill in the art for other proteins and peptides, depending on the therapeutic label of choice, the choice of chelator the number of sites available for chelator attachment, susceptibility of the protein to radiolysis, desired level of efficacy, etc.

Any bifunctional chelator may be used in the method of the present invention so long as it is capable of binding to both the protein and radioisotope of interest. Preferred chelators may be selected from the group consisting of MX-DTPA, phenyl-DTPA, benzyl-DTPA, CHX-DTPA, DOTA and derivatives thereof. A particularly preferred chelator is MX-DTPA.

"Amiable conditions" as referenced in the present methods include acceptable temperature, pH and buffer conditions. It should be apparent to those of skill in the art that reaction conditions should not be chosen that are inhibitory or otherwise not conducive to the labeling reaction. Lewis et al. discusses reaction conditions to be considered when radiolabeling immunoconjugates, and is herein incorporated by reference (1994. A facile, water-soluble method for modification of proteins with DOTA. Use of elevated temperature and optimized pH to achieve high specific activity and high chelate stability in radiolabeled immunoconjugates. Bioconjugate Chem. 5: 565–576).

An acceptable temperature for the reaction may vary depending on the protein to be labeled, but in general ranges from about 25° C. to about 43° C. Lewis et al. have found that increasing the temperature of the radiolabeling reaction from 25° C. to 43° C. increased both the efficiency of radiometal incorporation and the kinetic stability of the DOTA radioconjugates examined.

An acceptable pH may vary considerably depending on the radiolabel to be used. The recommended pH for labeling with different radionuclides is generally known in the art and may be chosen accordingly in view of the radioisotope. For instance, for $^{90}Y$, an acceptable pH may range from about 3 to about 6, but is more preferably about 4.2.

Acceptable buffers will also vary depending on the particular radiolabel. For instance, Lewis et al. and others have found that the presence of citrate inhibits labeling reactions with $^{90}Y$. Thus, citrate buffer would not be appropriate if the $^{90}Y$ were the chosen radiolabel. When labeling with $^{90}Y$ the preferred buffer is an acetate buffer, and more particularly a sodium acetate buffer at a concentration of between about 10 and about 1000 mM.

If it does not inhibit or otherwise adversely affect the labeling reaction, it may also be possible for a benign (non-adverse) radioprotectant to be included in the reaction buffer. According to Chakrabarti, ascorbic acid is one such radioprotectant which does not interfere with the labeling process. Caution should be exercised, however, when employing human serum albumin in the labeling reaction due to the presence of metals which would interfere with the labeling process. HSA (as well as other radioprotectants) may need to be treated to lower metal content so that acceptable incorporation is obtained.

Because the present invention concerns radiolabeling proteins with particularly radiolytic isotopes, there may be a certain balance between binding specificity and specific activity that the skilled artisan may encounter when practicing the methods of the present invention. For instance, when specific activity is very high (i.e., suitably over 5 mCi/mg, preferably over 10 mCi/mg and more preferably over 15 mCi/mg), a protein construct having the desired binding specificity will have a significant killing capability at the region of the tumor. However, the portion of proteins in the population as a whole which retain their immunoreactivity may be lower than a population having a lower specific activity due to radiolysis of the radiolabel. Depending on the desired level of specific activity, the skilled artisan may choose to compromise a certain level of immunoreactivity.

For instance, the present inventors have found that, with $^{90}Y$, when an antibody is labeled to a specific activity of about 15 mCi/mg, the binding specificity or immunoreactivity of the protein is generally at least about 70%. This of course may vary depending on the sensitivity of the antibody and the radiolytic nature of the radioisotope employed, and may be manipulated by the skilled artisan if a higher level of immunoreactivity or specific activity is desired. The present inventors have achieved specific activities with $^{90}Y$ of up to about 20 mCi/mg. Binding specificities of at least 50% are desirable for therapeutic applications.

U.S. patent application Ser. No. 09/259,337 (abandoned in favor of pending U.S. patent application Ser. No. 11/033, 439) and U.S. patent application Ser. No 09/259,347 (issued as U.S. Pat. No. 6,300,143), co-owned and submitted concurrently herewith, disclose binding assays which may be used to assess the percent binding affinity and immunoreactivity of conjugates after labeling if desirable. It should be stressed that, although no further purification is required after the labeling methods of the present invention, a TLC-based assay to verify the level of radioincorporation should always be performed so as not to jeopardize the health of the patient. Such an assay can be performed in about 3–4 minutes, and should not significantly affect the stability or efficacy of the radiotherapeutic.

The present invention also includes kits for radiolabeling a chelator-conjugated protein or peptide with a therapeutic radioisotope for administration to a patient comprising (i) a vial containing chelator-conjugated protein or peptide, (ii) a vial containing formulation buffer for stabilizing and administering the radiolabeled antibody to a patient, and (iii) instructions for performing the radiolabeling procedure, such that when the chelator-conjugated protein or peptide is exposed to the radioisotope or a salt thereof for a sufficient amount of time under amiable conditions as recommended in said instructions and described further above, a radiolabeled protein or peptide having sufficient purity, specific activity and binding specificity is achieved such that the radiolabeled antibody may be diluted to an appropriate concentration in said formulation buffer and administered directly to the patient without further purification. Said chelator-conjugated protein or peptide may be supplied in lyophilized form.

It should be understood that the kits of the present invent are designed to accomplish the methods described herein and may therefor be used for that purpose. Accordingly, it should be apparent to those concerned when reading the invention that the kit instructions will be based on the methods described above, and that the considerations addressed above have the same relevance and meaning when considered in view of the kit embodiment. Additionally, it should be apparent upon reading the disclosure as a whole that alternative kit embodiments are encompassed in the present invention which may contain components such as an acetate buffer for adjusting the pH of the radioisotope or of the protein as described above.

A particularly advantageous component of the kit is the formulation buffer for stabilizing against the effects of radiolysis and administering the radiolabeled conjugated antibody to a patient. The formulation buffer is a pharmaceutically acceptable carrier which serves as both a diluent for the labeled antibody and an administration buffer. Although any pharmaceutically acceptable diluent may be used for administering therapeutic or diagnostic antibodies to patient, the formulation buffer of the present invention is particularly suited for administering radiolabeled antibodies.

For instance, the formulation buffer of the present invention comprises a radioprotectant such as human serum albumin (HSA) or ascorbate, which minimize radiolysis due to yttrium and other strong radionuclides. Other radioprotectants are known in the art and could also be used in the formulation buffer of the present invention, i.e., free radical scavengers (phenol, sulfites, glutathione, cysteine, gentisic acid, nicotinic acid, ascorbyl palmitate, HOP(:O)H$_2$, glycerol, sodium formaldehyde sulfoxylate, $Na_2S_2O_5$, $Na_2S_2O_3$, and $SO_2$, etc.).

The formulation buffer of the present invention also comprises excess unconjugated chelator. The purpose for including unconjugated chelator is that this chelator serves to scavenge any non-protein bound radiolabel in the patient, and causes excretion of the radiolabel thereby reducing uptake of "bone-seeking" isotopes, i.e., $^{90}Y$, by the bones of the patient. For instance, when the antibody of the kit is conjugated to a DTPA chelator, excess DTPA or any other chelator may be included in the formulation buffer. The formation buffer is also preferably supplied in a volume such that the entire contents are transferred to the reaction vial. As discussed above, this results in increased ease of use and reproducibility because exact volumes do not have to be measured and transferred.

A preferred formulation buffer comprises phosphate buffered or physiological saline, human serum albumin and DTPA. The human serum albumin is preferably at a concentration of between about 5 to 25% (w/v), and more preferably at a concentration of about 7.5% (w/v). The concentration of DTPA is preferably about 1 mM. Ascorbate may be used as an alternative to human serum albumin, and is typically used at a concentration of about 1 to 100 mg/ml. Although a wider range of concentrations may be used without compromising patient safety.

The kit may be supplied in other alternative embodiments depending on the preferences of the purchaser. For instance, the kit may further comprise a sterile reaction vial in which the labeling reaction and dilution into formulation buffer may both be performed. Further embodiments are envisioned whereby the buffer for adjusting the pH of the radiolabel is supplied in the actual reaction vial to cut down on waste and increase ease-of-use. Also, envisioned is a kit where isotope is provided in a "buffered" form allowing for direct addition of the antibody/peptide conjugate to the isotope vial which serves as a reaction vial. Also, the conjugate could be provided in a "buffered" form allowing direct addition of isotope. Thus, included in the invention are kits which further comprise a vial of radioisotope, although it may be more feasible to order the labeling kit in advance and order the radioisotope separately at a later time just before administration. Also envisioned are kits which comprise a vial of secondary protein or peptide to serve as either a control in assessing the binding affinity of the radiolabeled product, or in some cases to be employed in a combined therapeutic regimen with the radiolabeled protein or peptide.

DETAILED DESCRIPTION OF THE PREFERRED EMBODIMENTS

A $^{90}Y$-labeled murine monoclonal anti-CD20 antibody (Y2B8) is currently being evaluated in clinical trials for the treatment of relapsed B-cell lymphoma. The 2B8 antibody is a murine antibody which recognizes human CD20. The chimeric version of this antibody (Rituxan®) has recently received FDA approval for the treatment of non-Hodgkin's lymphoma. U.S. application Ser. No. 08/475,813, herein incorporated by reference, discloses sequential administration of Rituxan® with yttrium-labeled murine monoclonal antibody in a combined therapeutic regimen, wherein administration of the yttrium-labeled anti-CD20 antibody following administration of Rituxan® is sufficient to (a) clear any remaining peripheral blood B cells not cleared by the chimeric anti-CD20 antibody; (b) begin B cell depletion from lymph nodes; or (c) begin B cell depletion from other tissues.

Thus, given the proven efficacy of an anti-CD20 antibody in the treatment of non-Hodgkin's lymphoma, and the known sensitivity of lymphocytes to radioactivity, it would be highly advantageous for such therapeutic antibodies to become commercially available in kit form whereby they may be readily modified with a radiolabel and administered directly to the patient in the clinical setting.

A radiolabeling kit for the 2B8 antibody is preferably comprised of four components: 1.) 2B8-MX-DTPA in low-metal normal saline at 2 mg/mL, 2.) 50 mM sodium acetate used to adjust radioisotope solution to appropriate labeling pH, 3.) formulation buffer (1×PBS, pH 7.4 containing 7.5% human serum albumin and 1 mM DTPA), and optionally, 4.) an empty 10 mL glass vial (reaction vial)(a "10 mL" reaction vial actually holds 10 mL comfortably, and is technically somewhat larger than "10 mL"). All components are tested to be sterile and pyrogen-free.

This section summarizes the validation of this radiolabeling kit which is simple and easy to use and which yields radiolabeled antibodies with ≧95% radioincorporation and acceptable retention of binding to antigen-positive cells. An evaluation of experimental parameters affecting binding and radioincorporation was also conducted.

EXAMPLE 1

Radiolabeling Kit and Method for Labeling 2B8 with $^{90}Y$

A. Reagents in Radiolabeling Kit
1. 2B8-MX-DTPA, IDEC; Lot# 082395RM2
2. 50 mM Sodium Acetate, low-metal, IDEC; Lot# 082395RM3
3. Formulation Buffer (1×PBS, pH 7.4 containing 7.5% (w/v) human serum albumin and 1 mM DTPA), IDEC, Lot# 082395RM1
4. Reaction vial, 10 mL, IDEC B. Materials and Equipment
1. Biodex Tec-Control Radioincorporation Kit, Cat.#151-770
2. Gloves: powder-free
3. Sterile polypropylene syringes
4. Sterile syringe needles
5. Small tubes with closure; 1.5 ml C. Methods
1. Preparation of Y2B8 Using Radiolabeling Kit Kit reagents were prepared and filled into glass septum vials. Type I borosilicate vials (2 or 10 mL) were rinsed with sterile water for injection (WFI) and autoclaved before filling. Butyl rubber septa were rinsed with sterile WFI and autoclaved before use. Reagents were manually filled and crimped in a Class 100 room and tested for pyrogenicity and sterility using USP methods.

Additional Reagents:
1. Yttrium-[90]: chloride salt, carrier-free, in HCl.

Precautions:
1. All steps should be performed using aseptic technique.
2. Radiolabeling kit components should be allowed to come to room temperature before use.

Radiolabeling Protocol
1. The volume of $^{90}YCl_3$ to add to the reaction vial was calculated as follows:
   a. The radioactivity concentration at the time of radiolabeling:
   $C_0$=Radioactivity concentration at time of calibration (see manufacturer's Certificate of Analysis).
   $\Delta t$=Change in time (positive number is post calibration, negative number is pre calibration).

$$\text{Radioactivity Concentration at time of labeling} = \frac{C_0}{e^{0.0108(\Delta t)}}$$

b. The volume of $^{90}YCl_3$ to add to the reaction vial:

$$\frac{45\, mCi}{\text{Radioactivity Concentration time of labeling}} = \text{Volume added to reaction vial}$$

2. The volume of 50 mM sodium acetate to add to the reaction vial was calculated as follows:
   a. For $^{90}YCl_3$ in 0.040 M HCL (Amersham):
   Volume $^{90}YCl_3$ (Step 1b)×(0.8)=volume of sodium acetate to add
   b. For $^{90}YCl_3$ in 0.050 M HCl(Nordion):
   Volume $^{90}YCl_3$ (Step 1)×(1.0)=volume of sodium acetate to add 3. The septa of the reaction vial and the sodium acetate vial were wiped with alcohol. Using a 1 cc syringe, the calculated volume (Step 1a or 1b) of 50 mM sodium acetate (Step 2) was transferred to the reaction vial. The vial was mixed by inverting several times.
4. The septum of the $^{90}YCl_3$ source vial was wiped with alcohol. The vial with a needle fitted with sterile 0.2 μm filter. Using a 1 cc sterile syringe, was vented the required volume (Step 1b) of $^{90}YCl_3$ was transferred to the reaction vial. The vial was mixed by inverting several times.
5. The septum of the 2B8-MX-DTPA vial was wiped with alcohol. Using a 3 cc sterile syringe, 1.5 mL of 2B8-MX-DTPA was transferred to the reaction vial. The vial was mixed by inverting several times.
6. The total volume of reaction mixture was calculated by adding the amount of Y-90 chloride added (Step 4), plus the amount of 50 mM sodium acetate added (Step 3), plus the amount of 2B8-MX-DTPA added (Step 5).
7. The volume of Formulation Buffer to add to the Reaction Vial to obtain a final volume of 10 mL was calculated by subtracting the total reaction volume calculated in step 6 from 10.
8. The Formulation Buffer vial was wiped with alcohol and the vial was vented. Due to the viscosity of the Formulation Buffer, the reaction vial using a needle fitted with a 0.20 μm syringe filter. Using a 10 cc sterile syringe fitted with an appropriate gauge needle, the volume of Formulation Buffer calculated in Step 7 was transferred to the reaction vial. The vent needle was removed from the reaction vial and the vial was mixed by inverting several times (Final Product). The vial was incubated at least 5 minutes prior to doing the "Radioincorporation Assay". The color of the solution was amber and the reaction vial was full thereby confirming that Formulation Buffer was added.
9. The total radioactivity of the Final Product vial was measured using the appropriate instrumentation set for measurement of $^{90}Y$.
10. The Final Product was immediately stored at 2°–8° C. until required for patient administration.

2. Radioincorporation Assay

Percent radioincorporation was determined by instant thin-layer chromatography (ITLC) using the Biodex Tec-Control Radiochromatographic Kit according to the following protocol:

Additional Materials and Equipment:
1. $^{90}Y$-radiolabeled 2B8-MX-DTPA
2. Tubes for counting radioactive TLC strips
3. Scissors
4. Sterile syringe, 1 cc
5. Sterile needles, 26 G
6. Gamma counter or scintillation counter
7. Pipettor Procedure:
1. The entire Biodex Operation Manual should be read first.
2. Each radiolabeled sample in triplicate was tested according to kit instructions; one strip per vial was developed.
3. To spot the radiolabeled sample on the chromatography strip, a pipettor was used to spot 1 μl on the origin line. Alternatively, one small drop dispensed from a 26 G needle attached to a sterile 1 cc syringe may be spotted. The antibody remains at the origin, and unincorporated $^{90}Y$-DTPA moves with the solvent front.
4. Each section was counted for activity using an appropriate counter, i.e., a scintillation counter for $^{90}Y$, adjusting for background.

5. The Biodex instructions for calculating the percentage of radiolabeled antibody were followed.

3. Binding Assay

Additional Reagents
1. $^{90}$Y2B8-MX-DTPA
2. Lyophilized cells

The human cell lines SB (CD20-positive) and HSB (CD20-negative) were obtained from American Type Culture Collection and cultured in T-flasks using RPMI-1640 containing 10% fetal bovine serum supplemented with 2% glutamine. Cultures were maintained at 37° C. and 5% $CO_2$. Cells were typically split 1:2 every other day and harvested at 0.5–2.5×10$^6$ cells/mL and viability's >80%. Cell concentrations were determined using a hemacytometer and viability determined by trypan blue exclusion.

Cells were harvested at ambient temperature at a cell density of 0.5–2×10$^6$ cells/ml by centrifugation (1300 rpm in a Sorvall centrifuge) and washed twice with 1×HBSS. Pelleted cells were resuspended to 50×10$^6$ cells/mL in 1×HBSS containing 1% (w/v) bovine serum albumin (BSA) and 10% (w/v/) mannitol (lyophilization buffer), 0.5 mL dispensed into 1.5 mL polypropylene microfuge tubes with o-ring gaskets and stored at −70° C., and lyophilized overnight at 30–60 millitorr. Tubes of lyophilized cells were stored desiccated at 2–8° C. and reconstituted in sterile water for assays; tubes of cells lyophilized in microfuge tubes were stored with desiccant.

3. Sterile water for irrigation or sterile water for injection
4. Dilution buffer (1×PBS, pH 7.2–7.4 containing 1% Bovine Serum Albumin (BSA), and 0.02% Sodium Azide)

Procedure:

Radiolabeled Antibody Sample Prep
1. The radiolabeled antibody stored at 2°–8° C. was obtained.
2. A volume of 10 µL was withdrawn with a P20 and added to a 1.5 mL microfuge tube containing 990 µL of Dilution buffer (1:100 dilution). The tip was rinsed and the tube was vortexed slightly.
3. A 50 mL sterile polypropylene tube with cap was obtained and 10 mL of Dilution buffer to the tube, using a 10 mL serological pipette.
4. A volume of 35 µL was withdrawn with a P200 from the 1:100 dilution tube and added to the conical tube containing 10 mL of Dilution buffer. Mix thoroughly.

Lyophilized Cell Prep
1. Three tubes of lyophilized SB Cells were obtained.
2. A volume of 0.5 mL of SWFI was added to each tube, and the tubes were vortexed until single cell suspensions were obtained.
3. Three empty 1.5 mL microfuge tubes were obtained; to three of the tubes, 0.5 mL of Dilution buffer was added, representing a control with no cells.

Assay Protocol
1. A volume of 0.5 mL of the diluted $^{90}$Y2B8-MX-DTPA was added to each tube.
2. The tubes were placed on end over mixer for 45 minutes, after making sure caps are securely tightened.
3. After 45 minutes incubation at ambient temperature, the cells were pelleted by microcentifugation for 5 minutes.
4. A volume of 0.8 mL of the supernatant was transferred to scintillation vials.
5. Scintillation cocktail was added to each vial.
6. The amount of radioactivity in each vial was determined using a scintillation counter, adjusting for background.

D. Results

Reproducibility and ruggedness of the radiolabeling protocols for Y2B8 was evaluated by performing several validation runs using different lots of each radioisotope. Six validation lots each of Y2B8 were prepared by five operators. These lots were designated as follows and performed at the following facilities:

1: IDEC Pharmaceuticals
2: IDEC Pharmaceuticals
3: IDEC Pharmaceuticals
4: MD Anderson Health Center
5: Mayo Clinic
6: City of Hope The results of testing on each validation lot are summarized in Table 1.

TABLE 1

Release Assay Results for Y2B8 Validation

| Lot Number | % Radioincorporation | % Binding |
|---|---|---|
| 1 | 99.5 | 78.6 |
| 2 | 99.3 | 87.0 |
| 3 | 99.4 | 85.9 |
| 4 | 99.2 | 81.8 |
| 5 | 99.2 | 79.6 |
| 6 | 96.3 | 80.8 |

Mean = 98.8  Mean = 82.3
Standard Deviation = 1.24  Standard Deviation = 3.4
% CV = 1.25%  CV = 4.2%

For the six validation lots prepared, the percent binding obtained was in the ranged from 78.6% to 87.0% with a mean of 82.3%. Radioincorporation values for Y2B8 averaged 98.8% (range of 96.3% to 99.5%). Together, these results confirm the reproducibility and ruggedness of the radiolabeling kit methods for preparation of Y2B8, and together indicate that Y2B8 prepared using this radiolabeling kit are suitable for use in the clinical setting.

EXAMPLE 2

Initial Evaluation of the Reaction Parameters-pH and Reaction Time

Kinetic studies were initially performed to evaluate the radioincorporation and binding of the $^{90}$Y-labeled antibody (Y2B8) following labeling reactions performed under varying conditions of pH and reaction time. For radiolabeling reactions in the range of pH 3.9 to 4.7 at an incubation time of 5 min, radioincorporation was >96% with >80% retention of binding to CD20-positive cells (Table 2). Similar results were obtained for incubation times of 3, 5, and 10 min for the range of pH 2.9 to 4.6 (Table 3).

TABLE 2

Y2B8 Radiolabeling Kinetics: Effect of pH on Radioincorporation and Binding to CD20-Positive Cells[1]

| Reaction pH | Radioincorporation (%) | Binding (%) |
|---|---|---|
| 3.9 | 98.4 | 80.7 |
| 4.2 | 97.8 | 81.0 |
| 4.4 | 96.1 | 80.0 |
| 4.6 | 97.0 | 80.2 |
| 4.7 | 97.4 | 80.6 |

TABLE 3

Y2B8 Radiolabeling Kinetics: Effect of Incubation Time on
Radioincorporation and Binding to CD20-Positive Cells[1]

| Incubation Time (min) | | Radioincorporation (%) | Binding (%) |
|---|---|---|---|
| pH 3.9: | 3 | 97.0 | 82.0 |
| | 5 | 98.9 | 82.1 |
| | 10 | 99.2 | 82.3 |
| pH 4.7: | 3 | 97.2 | 82.5 |
| | 5 | 96.7 | 81.8 |
| | 10 | 97.6 | 81.5 |

[1]The labeling reaction results and parameter evaluation studies reported in Tables 2 and 3 were performed with 2B8 derived from a CHO cell expression system; The MX-DTPA conjugate was prepared using a protocol similar to that used for the previously characterized 2B8-49.Reactions were performed using approximately 3 mg of antibody and a 4:1 molar ratio of chelator to antibody as described in co-owned, copending Application Serial No. 09/259,337, concurrently filed and herein incorporated by reference.

Immunoreactivities for Y2B8 preparations were determined using the method of Lindmo et al. Increasing amounts of freshly harvested CD20-positive SB cells were incubated with a fixed amount of Y2B8 under conditions of antigen excess. Reciprocal plot analysis of the binding data showed an immunoreactivity of 72.2% for Y2B8 following one trial preparation (FIG. 1).

EXAMPLE 3

Evaluation of Further Reaction Parameters

I. Introduction

Experiments described in this section examine the impact of protocol deviations on the binding of Y2B8 prepared using the Y2B8 Radiolabeling Kit. Binding of a radiolabeled antibody may be affected by several parameters during the radiolabeling process (Table 4).

TABLE 4

| Radiolabeling Kit Deviation | Predicted Effect on Labeling Conditions | Predicted Effect on Binding |
|---|---|---|
| 1.) Adding Excess Volume of $^{90}$Y | decrease pH; increase radiolysis | decrease |
| 2.) Adding Less Volume of $^{90}$Y | no change in pH; decrease radiolysis | increase or none |
| 3.) Adding Excess Volume of NaAc | no change in pH; decrease radiolysis | increase or none |
| 4.) Adding Less Volume of NaAc | decrease pH; increase radiolysis | decrease |
| 5.) Adding Excess Volume of 2B8-MX-DTPA | no change in pH; decrease radiolysis (lower specific activity) | increase |
| 6.) Adding Less Volume of 2B8-MX-DTPA | no change in pH; increase radiolysis (higher specific activity) | decrease |
| 7.) Incubating >5 min. | increase radiolysis | decrease |
| 8.) Incubating <5 min. | decrease radiolysis | increase or none |

The following deviations from the radiolabeling protocol were identified as those most likely to have a negative impact on binding, and included: 1.) addition of a lesser volume of sodium acetate 2.) addition of excess $^{90}$Y chloride solution 3.) addition of a lesser volume of 2B8-MX DTPA and 4.) exceeding the maximum reaction incubation time. The impact of these deviations was evaluated separately and simultaneously.

When evaluated separately, 20% volume deviations in items 1–3 above resulted in IDEC-Y2B8 passing the release specification established for binding in the clinical trial, even when incubated for 8 min. In a study where all three volume deviations (1–3 above) were made simultaneously, only doses prepared using a Monday labeling protocol (potentially the most radiolytic) and incubated for 8 min. (60% longer than normal) were marginally below (<3%) the clinical release specification. In contrast, doses prepared using a Friday labeling protocol maintained acceptable binding results, despite the cumulative effects of deviations in all four parameters (1–4 above). For all deviations, separately and collectively, radioincorporation was above the clinical release specification of 95%.

II. Choice of Parameters

We decided that a 20% deviation from the required reagent volumes, or allowing the reaction time to exceed by 30% the maximum 6 min. used normally, represented potentially extreme deviations from the protocol used in the radiopharmacy. In this study we evaluate the impact of these deviations on the binding of IDEC-Y2B8. We simulated "Monday" and "Friday" labelings to insure that the conditions evaluated represented extremes of dose preparation for the entire week. We also evaluated the combined effect on binding when all deviations occur in a single dose preparation, and the impact of these deviations on radioincorporation of the $^{90}$Y.

"Monday" and "Friday" labelings are a reflection of the concept that, since the $^{90}$Y chloride solution has a short half-life (64 hr), the volume of the radioisotope used depends on the day of the week a dose is prepared. For this reason, the reaction volume for a dose prepared on a Monday is smaller, resulting in higher a $^{90}$Y concentration, possibly resulting in greater radiolysis. Therefore, we simulated Monday and Friday labeling procedures to insure that the conditions evaluated represented extremes of dose preparation for the entire week.

III. Materials and Methods

A. Reagents
1. $^{90}$YCl$_3$ in 0.05 M HCL; Pacific Northwest National Laboratory, reagent grade; P.O.# 08016, 08118
2. Ultrex HCL; J. T. Baker, Product# 6900, Lot# J22539
3. Sterile Water for Irrigation; Baxter, Part# 2F7114, Lot# G924092
4. Dilution Buffer; contains 10 mM phosphate buffered saline, pH 7.4, 1% BSA; Sigma, Part# P-3688, Lot# 076H8913
5. IDEC Supplied Radiolabeling Kit; IDEC Part# 130018, Lot# 0129, containing the following:
   a.) 2B8-MX-DTPA; IDEC Part# 129017, Lot# 0165
   b.) 50 mM Sodium Acetate; IDEC Part# 121017, Lot# 0209A
   c.) Formulation Buffer; IDEC Part# 120015, Lot# 0202
   d.) Reaction Vial; IDEC Part# 122015, Lot# 0218
6. Lyophilized SB Cells, IDEC Part# 127, Lot# 127-001F B Materials and Equipment
1. Pipettors (20, 200 and 1000 gL)
2. Vortexer
3. Metal-Free Pipette Tips (Biorad; metal-free)
4. Gamma Counter (Isodata, Model# 20-10)
5. Glass Tubes (12×75 mm)

6. Polypropylene Tubes (Costar; 15 mL and 50 mL conical, sterile)
7. Tec-Control Radiochromatographic Kit (Biodex; Cat# 151-770)
8. Microcentrifuge (Savant)
9. Polypropylene microfuge tubes, metal-free (Biorad; Cat# 223-9480)

C. Methods

1. Preparation of Y2B8

In general, $^{90}$Y-labeled 2B8-MX-DTPA was prepared using a small-scale version of the radiolabeling kit protocol described above as modified by the changes described below. Radiolabeling was performed using $^{90}$Y chloride stock concentrations of 84 mCi/mL or 29.8 mCi/mL to simulate, respectively, Monday or Friday dose preparations (based on a Wednesday calibration of 50 mCi/mL). The concentrated $^{90}$Y chloride solution was diluted using 50 mM HCl (Ultrex, high-purity) in plastic "metal-free" microfuge tubes. The Ultrex (high-purity) HCl was diluted to 50 mM with Sterile Water for Irrigation (SWFI). Radiolabeling reactions were performed in plastic "metal-free" microfuge tubes, 15 mL conical tubes, or 10 mL glass septum Reaction Vial provided in the Y2B8 Radiolabeling Kit.

a. Small-Scale Labeling to Predict Full-Scale Dose Preparations

Radiolabeling reactions of 1, 3, 10, and 40 mCi were performed using reaction conditions simulating a Monday dose preparation. Reagent volumes in mLs for each reaction are summarized in Table 5.

TABLE 5

| | Volume of Reagents (mL) | | |
|---|---|---|---|
| $^{90}$Y Amount (mCi) | $^{90}$Y Chloride | Sodium Acetate | 2B8-MX-DTPA |
| 1 | 0.0119 | 0.0143 | 0.0333 |
| 3 | 0.0357 | 0.0429 | 0.0998 |
| 10 | 0.119 | 0.143 | 0.333 |
| 40 | 0.476 | 0.571 | 1.33 |

After a 5 min. incubation, 20 µL samples were removed and diluted with Formulation buffer to a final antibody concentration of 0.21 mg/mL and stored at 2–8° C. until assayed. Binding values were normalized to the 1 mCi reaction because 1 mCi reactions were used as controls in all subsequent experiments described in this report. Values reported were normalized to the 1 mCi control sample by dividing the binding value for each reaction by the binding value for the control, expressed as a percentage.

b. Impact of Adding Volume of Sodium Acetate

For a Monday labeling, 10 mCi of $^{90}$Y chloride (0.119 mL) was mixed with 0.114 mL of 50 mM sodium acetate. This volume of 50 mM sodium acetate represents a 20% decrease in the amount of buffer normally used to prepare clinical doses of IDEC-Y2B8. Conjugated antibody (2B8-MX-DTPA) was added (0.333 mL), the sample mixed and then incubated at ambient temperature. Specific activity of the radiolabeling solution was 18.9 mCi/mg antibody. At 2 min., 0.020 mL was removed, formulated to 0.24 mg/mL with formulation buffer, and stored at 2–8° C. The remainder of the radiolabeling solution was formulated, after 8 min., to 0.24 mg/mL and stored at 2–8° C. The protocol was repeated to simulate a Friday labeling, using 0.336 mL of $^{90}$Y chloride, 0.323 mL of sodium acetate, and 0.333 mL of 2B8-MX-DTPA. For both studies, the 1 mCi control reaction was performed using the "standard" conditions described above (5 min. reaction).

c. Impact of Adding Excess Volume of $^{90}$Y Chloride

For a Monday labeling, 12 mCi of $^{90}$Y chloride (0.143 mL) mixed with 0.143 mL of 50 mM sodium acetate. This volume of $^{90}$Y represents a 20% increase in the amount of $^{90}$Y required for a typical dose preparation of Y2B8. Conjugated antibody was added and the sample solution mixed and incubated at ambient temperature. The final specific activity was 22.5 mCi/mg antibody. At 2 min., 0.020 mL was removed, formulated to 0.24 mg/mL with formulation buffer, and stored at 2–8° C. After 8 min., the remainder of the radiolabeling solution was formulated to 0.24 mg/mL and stored at 2–8° C. Friday labeling was performed similarly using 0.403 mL of $^{90}$Y chloride, 0.403 mL of 50 mM sodium acetate, and 0.333 mL of 2B8-MX-DTPA (specific activity 22.5 mCi/mg antibody). For both studies, a 1 mCi control reaction was performed using the "standard" conditions described above (5 min. reaction).

d. Impact of Adding Less Volume of Antibody Conjugate

For a Monday labeling, 10 mCi of $^{90}$Y chloride (0.119 mL) was mixed with 0.143 mL 50 mM sodium acetate. Conjugated antibody (0.267 mL) was added, representing 20% less antibody than normally used, the solution mixed and incubated at ambient temperature. At 2 and 8 min., 0.020 mL was removed, formulated with Formulation buffer to a final antibody concentration of 0.21 mg/mL and stored at 2–8° C. until assayed. A Friday labeling was performed similarly using 0.336 mL $^{90}$Y chloride, 0.403 mL of 50 mM sodium acetate, and 0.27 mL conjugate. For both studies, a 1 mCi control reaction was performed using the "standard" conditions described above (5 min. reaction).

e. Impact of Combined Reagent Deviations

The impact of a 20% deviation in volume of sodium acetate, $^{90}$Y chloride, and conjugate was assessed simultaneously for a Monday or a Friday labeling protocol. For a Monday labeling, 12 mCi of $^{90}$Y (0.143 mL) was mixed with 0.114 mL 50 mM sodium acetate, representing a 20% increase in the amount of $^{90}$Y chloride and a 20% decrease in the amount of sodium acetate normally used. 2B8-MX-DTPA (0.267 mL), representing 20% less antibody than normally used, was added and the reaction mixture incubated at ambient temperature. At 2, 4, 6, and 8 min., 0.020 mL was removed from the reaction mixture, formulated with Formulation buffer to a final antibody concentration of 0.21 mg/mL, and stored at 2–8° C. until assayed. Friday labeling was performed similarly using 0.403 mL $^{90}$Y chloride, 0.387 mL of sodium acetate, and 0.267 mL of conjugate; 40 µL samples were removed at the indicated times and formulated with Formulation buffer. For both studies, a 1 mCi control reaction was performed using the "standard" conditions described above (5 min. reaction).

2. Determination of Radioincorporation

The amount of radioactivity associated with the conjugates was determined according to the assay described above, using the commercially available kit manufactured by Biodex (Tec-Control Radiochromatographic Kit). In general, 0.5–1 µL samples were applied to duplicate strips using a micropipetter and developed according to the Biodex instructional insert. Strip halves were counted for radioactivity in glass tubes using an Isodata gamma counter with window to 100–1000 KeV. The radiolabel incorporation was calculated by dividing the amount of radioactivity in the top half of the strip by the total radioactivity found in both top and bottom halves. This value was expressed as a percentage and the mean value determined.

3. Determination of Binding

Samples were analyzed for percent binding to CD20 positive cells following the protocol described above. However, the negative control HSB Cell samples were not included in these experiments, and the SB Cells were lyophilized in 5 mL vials instead of microfuge tubes.

Essentially, all final formulated Y2B8 samples were diluted 1:100 with Dilution buffer (10.0 µL antibody+990 [µL buffer). The antibody was subsequently diluted again to an approximate concentration ranging of 8 ng/mL by adding 35 µL of the 1:100 dilution to 10 mL of dilution buffer in a 50 mL polypropylene tube.

Six to seven vials of lyophilized cells were reconstituted with SWFI and pooled in a 50 mL conical tube. Reconstituted cells (0.5 mL) were then aliquoted out in triplicate into three 1.5 mL microfuge tubes, three tubes per sample being tested. Dilution buffer (0.5 mL) was added to three empty microfuge tubes. Diluted antibody (0.5 mL) was added to each tube, capped tightly, and incubated at ambient temperature for 45 min. with end-over-end mixing. After incubation, cells were pelleted by centrifugation for 5 min. at a setting of "6" (4000×g) using a Savant microcentrifuge. Supernatants from the samples (0.75 mL) were transferred to 12×75 mm glass tubes for radioactivity counting using an Isodata gamma counter with energy window settings of 100–1000 KeV.

Radioactivity bound (B) to cells was calculated by subtracting the unbound radioactivity (supernatant) from the total radioactivity added. Total radioactivity was determined from the radioactivity counted in the tubes without cells. Percent binding was calculated by expressing the bound radioactivity as a percentage of the total.

To minimize the effect of lot-to-lot 'variability of lyophilized cells used to assess binding, binding values were normalized to 1 mCi Y2B8 controls prepared using "standard" labeling conditions. Control samples were prepared, as stated earlier in this section, for each set of experiments.

D. Results

1. Small-Scale Labeling to Predict Full-Scale Dose Preparations

To insure that small-scale radiolabeling reactions were predictive of full-scale (40 mCi) dose preparations, 1, 3, 10, and 40 mCi Y2B8 doses were prepared using the radiolabeling protocols described above. These results are shown in Table 6 and demonstrate that increasing the scale of the reaction mixture from 1 mCi to 40 mCi dose not adversely affect binding or radioincorporation.

TABLE 6

| Amount of $^{90}$Y mCi | % of Control Binding | % Radioincorporation |
| --- | --- | --- |
| 1 | 100 | 99.2 |
| 3 | 102 | 99.1 |
| 10 | 98.6 | 99.0 |
| 40 | 98.2 | 99.0 |

2. Impact of Adding Less Volume of Sodium Acetate

When Y2B8 was prepared using 20% less volume of 50 mM sodium acetate, and extending the incubation time by 60%, substantial binding was retained, compared to the radiolabeled antibody prepared following "standard" labeling conditions (Table 7 below). Even when the labeling reaction was performed using Monday labeling conditions, >89% of the control binding was retained. Similar results were obtained for a Friday dose preparation. These deviations did not impact radioincorporation, regardless of the day the dose was prepared.

3. Impact of Adding Excess Volume of $^{90}$Yttrium Chloride

When Y2B8 was prepared using a 20% excess volume of $^{90}$Y chloride, in combination with an incubation time 60% longer than that used normally, substantial binding was retained, when compared to the control prepared according to "standard" labeling conditions (Table 7 below). When the labeling reaction was increased to 8 min., binding still remained >90%, relative to the control, for either a Monday or a Friday dose preparation. Adding 20% more volume of $^{90}$Y chloride did not impact radioincorporation, regardless of the day the dose was prepared.

4. Impact of Adding Less Volume of Antibody Conjugate

When Y2B8 was prepared using a 20% less volume of the conjugate (2B8-MX-DTPA), and extending the incubation time by 60%,binding was not significantly affected, compared to Y2B8 prepared according to "standard" labeling conditions (Table 7 below). Adding 20% less volume of conjugate did not impact radioincorporation, regardless of the day the dose was prepared.

TABLE 7

| | Monday Dose Preparation[a] | | Friday Dose Preparation[b] | |
| --- | --- | --- | --- | --- |
| Labeling Deviation | % of Binding Control[b] | % Radioincorporation | % of Binding Control[b] | % Radioincorporation |
| 1.) 20% Less Volume of Sodium Acetate 2.) 60% Increase in Reaction Time (8 min.) | 89.4 | 99.1 | 92.5 | 98.7 |
| 1.) 20% Excess Volume of $^{90}$Y 2.) 60% Increase in Reaction Time (8 min.) | 90.6 | 99.1 | 91.8 | 98.6 |
| 1.) 20% Less Volume of Antibody | 98.9 | 99.0 | 98.7 | 98.6 |

TABLE 7-continued

| | Monday Dose Preparation[a] | | Friday Dose Preparation[b] | |
|---|---|---|---|---|
| Labeling Deviation | % of Binding Control[b] | % Radioincorporation | % of Binding Control[b] | % Radioincorporation |
| 2.) 60% Increase in Reaction Time (8 min.) | | | | |

[a] For a Monday dose preparation, the concentration of $^{90}$Y in the reaction solution is 17 mCi/mL; the $^{90}$Y concentration for a Friday labeling is 8 mCi/mL.
Binding values normalized to labeled antibody prepared according to clinical dose protocol (RSBR-005) using "standard" reagent volumes and a 5 min. reaction time.

5. Impact of Combined Reagent Deviations

When Y2B8 was prepared using a protocol in which all four deviations were made simultaneously, binding was still substantially maintained, compared to the radiolabeled antibody prepared using "standard" labeling conditions (Table 8 below). Binding was still >83%, even when a Monday preparation was incubated for 30% longer than the maximum 6 min. used normally. Radioincorporation was not affected significantly by these cumulative deviations, even after an 8 min. incubation time, regardless of the day the dose was prepared.

TABLE 8

| Labeling Time (min.) | % of Binding Control | % Radioincorporation |
|---|---|---|
| Monday Dose Preparation | | |
| 2 | 97.6 | 98.7 |
| 4 | 93.7 | 98.8 |
| 6 | 89.5 | 98.8 |
| 8 | 83.2 | 98.6 |
| Friday Dose Preparation | | |
| 2 | 98.6 | 99.0 |
| 4 | 98.5 | 99.2 |
| 6 | 96.0 | 99.1 |
| 8 | 92.1 | 99.1 |

V. Discussion

To reduce radiation exposure to operators, smaller labeling reactions were evaluated instead of full-scale dose preparations. Therefore, we verified that the 1 mCi and 10 mCi labelings, evaluated in this study, were predictive of full-scale 40 mCi preparations. Results demonstrated no significant differences in binding and radioincorporation over a range of 1 mCi to 40 mCi.

We decided that 20% volume errors for sodium acetate, $^{90}$Y chloride, and conjugated antibody represented potentially extreme deviations in the radiolabeling protocol. Additionally incubating for 8 min. (3 min. longer than normal) was viewed as a significant protocol deviation. In general, due to the short half life of $^{90}$Y chloride, the volume of radioisotope will differ depending on the day of the dose preparation. Therefore, experiments described in this report were performed using $^{90}$Y chloride at concentrations representative of both Monday and Friday to represent the full range of possible dose preparation.

Y2B8 doses prepared using 20% lesser volume of sodium acetate, and incubated for 8 min. retained significant binding (>89%) relative to the standard labeling conditions. Similar results were obtained for doses prepared Monday or Friday. This deviation in sodium acetate volume did not affect radioincorporation.

Adding 20% more volume of $^{90}$Y chloride, and incubating for up to 8 min., reduced binding, relative to standard dose preparation conditions, for both Monday and Friday. However, binding was still >90%, which is above the normalized release specification. Binding was marginally better for a Friday dose preparation. Radioincorporation was not significantly affected by the increased volume of $^{90}$Y chloride.

To evaluate the impact of making simultaneously all volume deviations, Monday and Friday doses were prepared comparing 2, 4, 6, and 8 min. incubation times. Only when Y2B8 was prepared on a Monday, using an 8 min. incubation time, does the binding marginally fail to meet the normalized specification (83.2% compared to the normalized release specification of 86.3%).

REFERENCES

Each of the following citations is herein incorporated by reference:

M. W. Brechbiel et al., "Synthesis of C-Functionalized trans-Cyclohexyldiethylenetriaminepenta-acetic Acids for Labelling of Monoclonal Antibodies with the Bismuth-212 αa-Particle Emitter", J. Chem. Soc. Perkin Trans., pp. 1173–1178, 1992

M. E. Izard et al., "An Improved Method for Labeling Monoclonal Antibodies with Samarium-153: Use of the Bifunctional Chelate 2-(p-Isothiocyanatobenzyl)-6-methyldiethylenetriaminepentaacetic Acid", Bioconjugate Chem., 3(4):346–350, 1992.

R. B. Huneke et al., "Effective α-Particle-mediated Radioimmunotherapy of Murine Leukemia[1]", Cancer Research, 52:5818–5820, 1992

O. A. Gansow et al., "Macrocyclic or Conventional Ligands? Selection of Effective Chelators for $^{90}$Y or $^{212}$Bi Radioimmunotherapy", Chemistry Section, Radiation Oncology Branch, Metabolism Branch, National Cancer Institute S. Mirzadeh[1,2] et al., "The Chemical Fate of $^{212}$Bi-DOTA Formed by β$^-$ Decay of $^{212}$Pb(DOTA)$^{2-*,**}$", Radiochimica Acta 60:1–10, 1993

What is claimed:

1. A method for radiolabeling a chelator-conjugated antibody or antibody fragment with $^{90}$Y for administration to a patient comprising:
   (i) mixing the chelator-conjugated antibody or antibody fragment with a solution comprising $^{90}$Y or a salt thereof, and
   (ii) incubating the mixture for a sufficient amount of time under amiable conditions such that a $^{90}$Y-labeled antibody or antibody fragment is produced having sufficient radioincorporation, immunoreactivity of at least 50%, and a specific activity of at least about 5 mCi/mg, such that the $^{90}$Y-labeled antibody or antibody fragment may be administered directly to the patient without further purification of the $^{90}$Y-labeled radiolabeled antibody or antibody fragment from unincorporated $^{90}$Y;

wherein said chelator is a bifunctional chelator selected from the group consisting of MX-DTPA, phenyl-DTPA, benzyl-DTPA, CHX-DTPA, DOTA and derivatives thereof.

2. The method of claim 1, wherein said amiable conditions refer to acceptable temperature, pH and buffer conditions.

3. The method of claim 2, wherein said acceptable temperature ranges from about 25° C. to about 50° C.

4. The method of claim 2, wherein said acceptable pH ranges from about 3 to about 6.

5. The method of claim 2, wherein said acceptable buffer is an acetate buffer and is at a concentration of between about 10 and about 1000 mM.

6. The method of claim 1, wherein said sufficient incubation time is less than about eight minutes.

7. The method of claim 6, wherein said sufficient incubation time is between about 30 seconds to about five minutes.

8. The method of claim 1, wherein the specific activity of the $^{90}$Y-labeled antibody or antibody fragment is greater than 10 mCi/mg.

9. The method of claim 8, wherein the specific activity of the $^{90}$Y-labeled antibody or antibody fragment is at least 15 mCimg.

10. The method of claim 1, wherein a level of radioincorporation of greater than 95% is achieved.

11. The method of claim 1, wherein a level of radioincorporation of greater than 96% is achieved.

12. The method of claim 1, wherein the immunoreactivity is at least 70%.

13. The method of claim 1, wherein the immunoreactivity is at least 80%.

14. The method of claim 1, wherein the chelator is MX-DTPA.

15. The method of claim 1, wherein the ratio of chelator to antibody or antibody fragment ranges from 1½ to 1.

16. The method of claim 1, wherein the antibody or antibody fragment binds specifically to CD20.

17. The method of claim 16, wherein the antibody is 2B8.

18. The method of claim 17, wherein the chelator is MX-DTPA.

19. The method of claim 1, wherein the antibody fragment is selected from the group consisting of Fab, F(ab')$_2$, and Fv fragments.

20. A method for radiolabeling a MX-DTPA-conjugated 2B8 antibody or antibody fragment with $^{90}$Y for administration to a patient comprising:

(i) mixing the MX-DTPA-conjugated antibody or antibody fragment with a solution comprising $^{90}$Y or a salt thereof, and (ii) incubating the mixture for a sufficient amount of time under acceptable temperature, pH and buffer conditions such that a $^{90}$Y-labeled antibody or antibody fragment is produced having sufficient radioincorporation, immunoreactivity of at least 50% , and a specific activity of at least about 5 mCi/mg, such that the $^{90}$Y-labeled antibody or antibody fragment may be administered directly to the patient without further purification of the $^{90}$Y-labeled 2B8 antibody or antibody fragment from unincorporated $^{90}$Y.

* * * * *